United States Patent [19]

Dow et al.

[11] Patent Number: 5,329,194
[45] Date of Patent: Jul. 12, 1994

[54] ULTRASONIC PERIPHERAL VASCULAR PROBE ASSEMBLY

[75] Inventors: Julian Dow, San Clemente; Paul F. Meyers, San Juan Capistrano; Michael Waddell, San Clemente, all of Calif.

[73] Assignee: Capistrano Labs, Inc., San Clemente, Calif.

[21] Appl. No.: 980,583

[22] Filed: Nov. 23, 1992

[51] Int. Cl.⁵ .............................................. H02K 33/00
[52] U.S. Cl. ....................................... 310/17; 310/28; 310/30
[58] Field of Search .............. 128/660.09, 660.10, 128/660.05, 662.03, 663.01, 662.04; 73/633, 625, 621, 861.25; 310/15, 17, 19, 21, 156, 68 B, 80, 28, 30

[56] References Cited

U.S. PATENT DOCUMENTS

| | | | |
|---|---|---|---|
| 3,955,561 | 5/1976 | Eggleton | 128/2.05 Z |
| 4,092,867 | 6/1978 | Matzuk | 73/609 |
| 4,106,346 | 8/1978 | Matzuk | 73/614 |
| 4,149,419 | 4/1979 | Connell et al. | |
| 4,246,792 | 1/1981 | Matzuk | 73/620 |
| 4,271,706 | 6/1981 | Ledley | 73/614 |
| 4,282,879 | 9/1981 | Kuni et al. | 128/660.09 |
| 4,341,120 | 7/1982 | Anderson | 128/660.09 |
| 4,375,818 | 3/1983 | Suwaki | 128/660 |
| 4,391,282 | 7/1983 | Ando et al. | 128/660 |
| 4,398,425 | 8/1983 | Matzuk | 73/633 |
| 4,399,703 | 8/1983 | Matzuk | 73/621 |
| 4,401,123 | 8/1983 | Baba | 128/660 |
| 4,421,118 | 12/1983 | Dow et al. | 128/660 |
| 4,424,813 | 1/1984 | Havlice et al. | 128/660 |
| 4,466,443 | 8/1984 | Utsugi | 128/660 |
| 4,479,388 | 10/1984 | Matzuk | 73/634 |
| 4,483,326 | 11/1984 | Yamaka | 128/4 |
| 4,545,117 | 10/1985 | Okamoto | 29/596 |
| 4,584,880 | 4/1986 | Matzuk | 73/609 |
| 4,646,722 | 3/1987 | Silverstein | 128/4 |
| 4,674,515 | 6/1987 | Andou et al. | 128/660 |
| 4,675,563 | 6/1987 | Goldowsky | 310/15 |
| 4,722,345 | 2/1988 | Shinichirou | 128/660 |
| 4,756,313 | 7/1988 | Terwilliger | 128/660 |
| 4,785,819 | 11/1988 | Pearce | 128/660.1 |
| 4,831,292 | 5/1989 | Berry | 310/15 |
| 4,841,979 | 6/1989 | Dow et al. | 128/660.1 |
| 4,850,362 | 7/1989 | Rello et al. | 128/660.09 |
| 4,893,628 | 1/1990 | Angelson | 128/660.05 |
| 4,913,155 | 4/1990 | Dow et al. | 128/660.1 |
| 5,012,147 | 4/1991 | Bertram et al. | 310/80 |
| 5,088,495 | 2/1992 | Miyagawa | 128/660.1 |
| 5,111,092 | 5/1992 | Reinicke | 310/68 B |

Primary Examiner—William E. Kamm
Assistant Examiner—George Manuel
Attorney, Agent, or Firm—Stetina and Brunda

[57] ABSTRACT

An ultrasonic probe has a housing, a base pivotally mounted within the housing, an extension formed upon the base, and a scanning ultrasonic transducer disposed upon the distal end of the extension. The extension is preferably configured such that the scanning transducer moves along an arc of approximately 50 degrees having a radius of approximately 40 mm and is thus suitable for imaging elongate anatomical structures such as portions of the peripheral vascular system. A doppler ultrasonic transducer fixedly disposed within the housing proximate the scanning ultrasonic transducer measures fluid flow within the elongate anatomical structure. The doppler ultrasonic transducer is disposed at one end of the arc along which the scanning ultrasonic transducer travels such that the radiation path of the doppler ultrasonic transducer is periodically obscured by the scanning ultrasonic transducer. The doppler ultrasonic transducer measures fluid flow through the elongate anatomical structure when the scanning ultrasonic transducer is not within the radiation path of the doppler ultrasonic transducer.

11 Claims, 3 Drawing Sheets

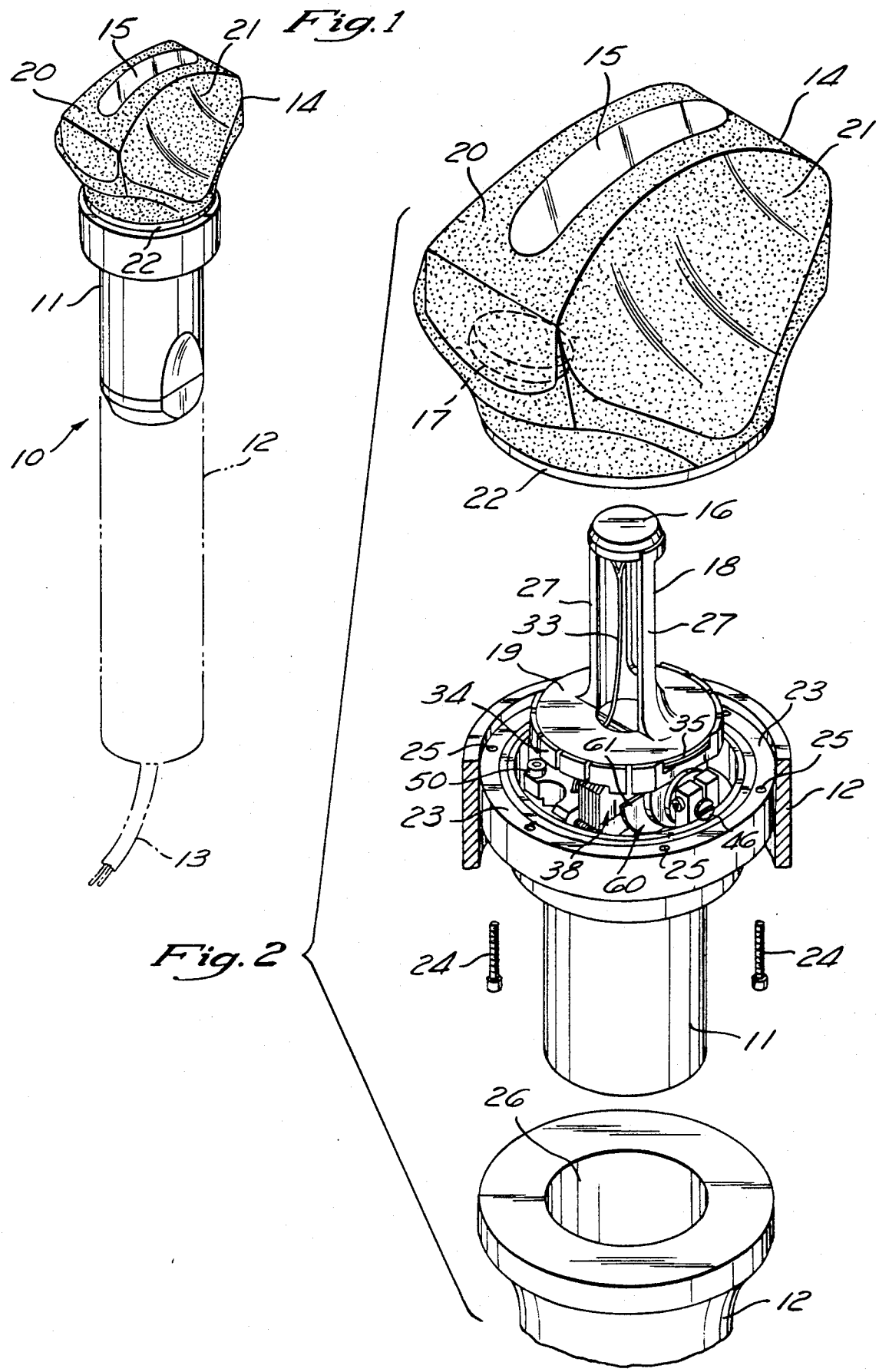

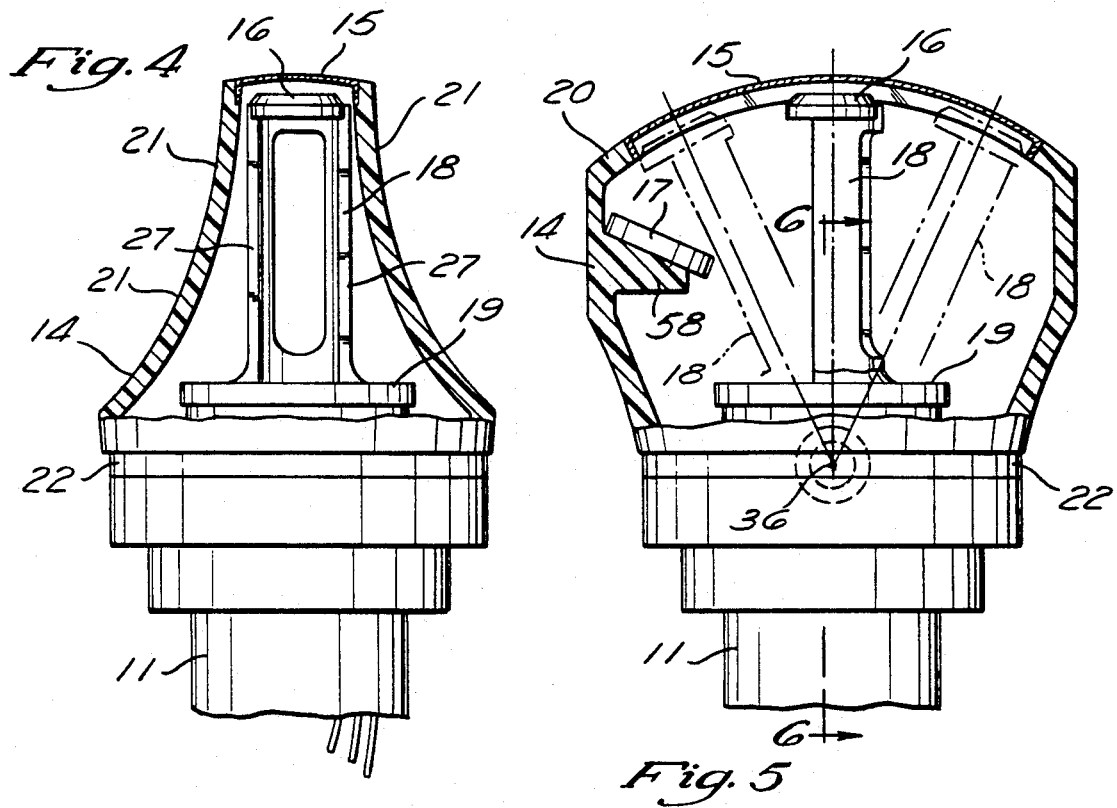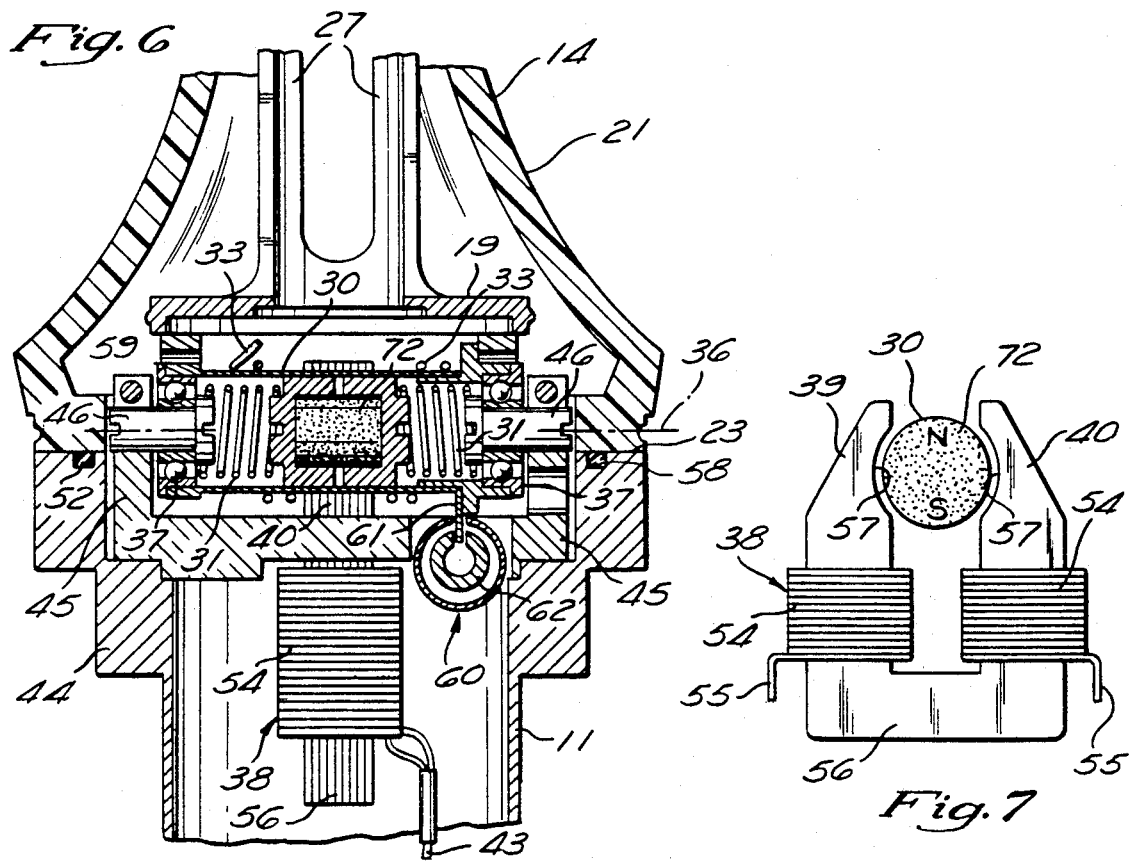

ULTRASONIC PERIPHERAL VASCULAR PROBE ASSEMBLY

FIELD OF THE INVENTION

The present invention relates generally to ultrasonic probe assemblies for use in real-time diagnostic imaging and relates more specifically to an ultrasonic probe assembly for real-time imaging of elongate anatomical structures and for simultaneously measuring the flow of fluid therethrough.

BACKGROUND OF THE INVENTION

In the field of ultrasonic diagnostics, acoustic images of anatomical structures are utilized in the diagnosis of various medical disorders. In order to produce real-time images of the anatomic structures, beams of ultrasonic energy from a probe are transmitted into the body tissue of a patient and echoes received by the ultrasonic probe are rapidly processed into an image format suitable for display. It is desirable that the probe produce an image over a wide field of view using a sector scan format. A sector scan format generates an image by repeatedly transmitting and receiving ultrasonic energy in radial directions away from the probe to define a fan-like pattern. The ultrasonic beam is directed by mechanically moving an ultrasonic transducer such that it is swept through an arc about a pivot axis to produce the fan-like sector scan pattern.

The prior art is replete with examples of ultrasonic transducer probe assemblies, such as those disclosed in U.S. Pat. No. 4,149,419 entitled "Ultrasonic Transducer Probe" issued Apr. 17, 1979 to R. Connell et al.; U.S. Pat No. 3,955,561 entitled "Cardioscan Probe" issued May 17, 1976 to R. Eggleton; U.S. Pat. No. 4,421,118 entitled "Ultrasonic Transducer" issued Dec. 20, 1983 to J. Dow et al.; U.S. Pat. No. 4,479,388 entitled "Ultrasonic Transducer and Drive System" issued on Oct. 30, 1984 to T. Matzuk; U.S. Pat. No. 4,399,703 entitled "Ultrasonic Transducer and Integral Drive Circuit Therefor" issued on Aug. 23, 1983 to T. Matzuk; U.S. Pat No. 4,092,867 entitled "Ultrasonic Scanning Apparatus" issued on Jun. 6, 1978 to T. Matzuk; U.S. Pat. No. 4,246,792 entitled "Self-Contained Ultrasonic Scanner" issued Jan. 27, 1981 to T. Matzuk; U.S. Pat. No. 4,398,425 entitled "Ultrasonic Scanning Transducer" issued on Aug. 16, 1983 to T. Matzuk; U.S. Pat No. 4,841,979 entitled "Ultrasonic Prostate Probe Assembly" issued on Jun. 27, 1989 to Dow et al.; and U.S. Pat. No. 4,913,155 entitled "Ultrasonic Transducer Probe Assembly" issued On Apr. 3, 1990 to Dow et al.

Although all of the above-referenced patent disclosures address various problems associated with the use of ultrasonic transducer imaging, none have addressed the particular problems associated with the use of an ultrasonic transducer probe for the imaging of elongate anatomical structures such as blood vessels in the peripheral vascular system. More particularly, none of the cited patent disclosures address the problem of measuring fluid flow through such an elongate anatomical structure while simultaneously providing real-time imaging of the structure.

It would be desirable to provide real-time imaging of portions of the peripheral vascular system and simultaneous measurements of the flow of blood therethrough. More particularly, it would be beneficial to provide real-time imaging of the carotid artery while simultaneously measuring the flow of blood therethrough in order to determine the presence of any pathologies, abnormal structures or conditions, and/or any indication of problems elsewhere within the vascular system, i.e., as provided by the blood flow rate.

Prior art ultrasonic probe assemblies have been ineffective in providing a satisfactory means for real-time imaging of elongate anatomical structures such as portions of the peripheral vascular system due to the sharp radius of curvature followed by the ultrasonic transducers thereof and additionally due to their inability to provide simultaneous blood flow measurements. The use of such a sharp radius of curvature is inherent in prior art devices due to the mounting of the ultrasonic transducer in immediate proximity to the pivot axis thereof. That is, the radius of the arc traveled by the ultrasonic transducer in such prior art devices is typically approximately 5–10 centimeters in length. Thus, the path traveled by the ultrasonic transducer is sharply curved and consequently suitable only for the imaging of comparatively small areas.

As such, although the prior art has recognized to a limited extent the problem ultrasonically imaging portions of the human anatomy, the proposed solutions have to date been ineffective in providing a satisfactory remedy.

SUMMARY OF THE INVENTION

The present invention specifically addresses and alleviates the above-mentioned deficiencies associated in the prior art. More particularly, the present invention comprises an ultrasonic probe having a housing, a base pivotally mounted within the housing, an extension formed upon the base, and a first or scanning ultrasonic transducer disposed Upon the distal end of the extension. The extension is preferably configured such that the scanning ultrasonic transducer moves along an arc of approximately fifty degrees having a radius of approximately 40 mm and an arc length of approximately 35 mm.

Thus, the present invention is especially well suited for the ultrasonic imaging of elongate anatomic structures such as peripheral blood vessels and the like. However, although the ultrasonic peripheral vascular probe assembly of the present invention is particularly well suited for imaging and blood flow measurement of the carotid artery, those skilled in the art will recognize that it is likewise suited for imaging and blood flow measurement of various other anatomical structures, including those which are not elongate in configuration.

A second or doppler ultrasonic transducer is fixedly disposed within the housing proximate the first ultrasonic transducer and utilizes the doppler effect to measure fluid flow within anatomical structures. The doppler ultrasonic transducer is disposed at one end of the arc along which the scanning ultrasonic transducer travels and thus the scanning ultrasonic transducer periodically obscures the radiation path of the doppler ultrasonic transducer. Such positioning of the doppler ultrasonic transducer thus minimizes the size of the probe. The doppler ultrasonic transducer consequently measures fluid flow through the anatomical structure being imaged only when the scanning ultrasonic transducer is not within the radiation path of the doppler ultrasonic transducer.

These, as well as other advantages of the present invention, will be more apparent from the following description and drawings. It is understood that changes in the specific structure shown and described may be made within the scope of the claims without departing from the spirit of the invention.

BRIEF DESCRIPTION OF THE DRAWINGS

FIG. 1 is a perspective view of the ultrasonic peripheral vascular probe assembly of the present invention with the handle portion shown in phantom;

FIG. 2 is an enlarged exploded perspective view of the upper portion of the ultrasonic peripheral vascular probe assembly of FIG. 1;

FIG. 4 is a side view, partially in cross-section, of the ultrasonic peripheral vascular probe assembly of FIGS. 1-3;

FIG. 5 is a side view, showing the ultrasonic peripheral vascular probe assembly of FIG. 4 rotated ninety degrees about its longitudinal axis and illustrating the scanning or reciprocating motion of the ultrasonic transducer;

FIG. 6 is an enlarged cross-sectional view of the motor or drive of FIG. 3; and

FIG. 7 is a schematic representation of the drive of FIG. 6.

DETAILED DESCRIPTION OF THE PREFERRED EMBODIMENT

Figure 3:
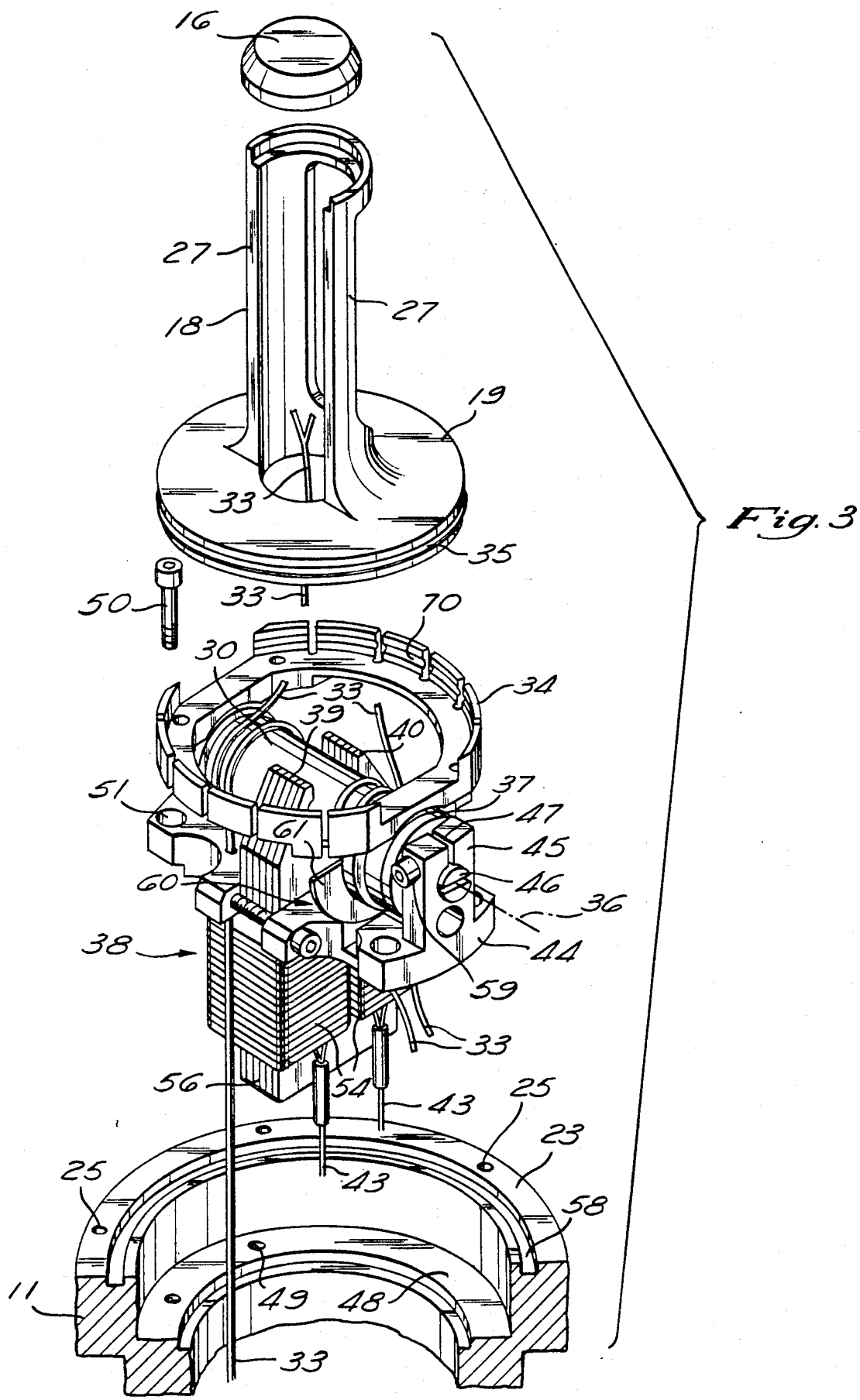
FIG. 3 is an enlarged exploded perspective view of the head assembly of FIG. 2.

The detailed description set forth below in connection with the appended drawings is intended as a description of the presently preferred embodiment of the invention, it is not intended to represent the only form in which the present invention may be constructed or utilized. The description sets forth the functions and sequence of steps for constructing and operating the invention in connection with the illustrated embodiment. It is to be understood, however, that the same or equivalent functions or sequences may be accomplished by different embodiments that are also intended to be encompassed within the spirit and scope of the invention.

The ultrasonic peripheral vascular probe assembly of the present invention is illustrated in FIGS. 1-7 which depict a presently preferred embodiment of the invention. Referring now to FIGS. 1 and 2, the ultrasonic peripheral vascular probe assembly 10 is comprised generally of a case or housing 11 having a handle 12 extending therefrom and a cap 14 attached thereto. A cable 13 extends from the housing and contains power, control and signal lines which interconnect the ultrasonic peripheral vascular probe assembly 10 with its associated power, control, and signal processing circuitry contained within a separate housing (not shown).

An elongate ultrasonic transparent window 15 is formed in the cap 14 to facilitate transmission of ultrasonic energy or radiation from first or scanning ultrasonic transducer 16 to the anatomical portion of the patient being scanned. Fluid contained with the cap 14 surrounds the first or scanning ultrasonic transducer 16 and facilitates transmission of ultrasonic energy from the scanning ultrasonic transducer 16 to the window 15.

To accommodate the elongate window 15, the cap 14 is formed in a complimentary elongate fashion and comprises a smooth, slightly arched upper surface 20 configured to comfortably and conveniently contact the patient. The sides 21 of the cap 14 are formed in a concave or scalloped configuration to minimize contact thereof with the patient such that the space occupied by the cap 14 is minimized, thus allowing the ultrasonic peripheral vascular probe assembly 10 of the present invention to be easily utilized in areas providing limited room. The neck 22 of the cap 14 forms a circular opening which abuts and seals against complimentary upper surface 23 of the housing 11. Fasteners, preferable screws 24 pass through apertures 25 formed in the housing 11 and thread into cap 14 to securely attach cap 14 thereto. Those skilled in the art will recognize that various other means for attachment are likewise suitable. A seal 52 (shown in FIG. 6) prevents leakage of the fluid from the cap 14. The handle 12 receives the lower portion of housing 11 into bore 26 (as shown in FIG. 2) thereof.

Referring now to FIGS. 3-6, the scanning ultrasonic transducer 16 is disposed atop post or extension 18, which is preferably hollow and/or comprises a plurality of individual column members 27 to minimize its mass. The extension 18 is formed upon base 19 which is configured to pivot reciprocally about the pivot axis 36 defined by armature 30 (best seen in FIG. 3) such that the scanning transducer moves along an arc, preferably of approximately 50 degrees and preferably having a radius of approximately 40 mm and an arc length of approximately 35 mm. Springs 31 urge the base 19 toward its center or non-driven position wherein the longitudinal axis of the extension 18 is generally co-aligned with the longitudinal axis of the case 11.

By positioning the scanning transducer 16 a sufficient distance from the pivot axis 36, the arc traveled by the scanning transducer 16 approximates straight line or linear motion such that movement of the scanning transducer 16 may be essentially along an elongate anatomical structure rather than merely at a point or comparatively small portion thereof as in prior art devices. That is, the scanning ultrasonic transducer 16 of the present invention tends to move back and forth along a line whereas in prior art devices the transducer merely pivots about a point and thus remains comparatively stationary. Thus, for the purposes of ultrasonic imaging, the path followed by the scanning ultrasonic transducer of the present invention is a substantially straight one.

In prior art devices the scanning ultrasonic transducer is positioned close, i.e. approximately 5-10 mm, to the pivot axis, thus movement of the scanning ultrasonic transducer is confined to a very limited area, essentially being slight pivoting or rocking about a point. In contrast, the scanning ultrasonic transducer 16 of the present invention moves reciprocally along a comparatively long arc which is approximately 40 mm from end to end. The scanning ultrasonic transducer 16 of the present invention thus covers a considerable area suitable for imaging of elongate anatomical structures, i.e. peripheral blood vessels, etc.

The doppler transducer 17 is fixedly mounted upon sensor base 58 which is preferably formed as an integral part of cap 14.

Wire 33 extends from the scanning ultrasonic transducer 16 through the extension 18 and wraps around armature 30, preferably approximately twice, to assure adequate strain relief thereof during reciprocating motion of the base 19. Wire 33 then extends through handle 12 and joins cable 13.

Base 19 attaches to base holder 34, preferably via a snap fit arrangement wherein male detent 35 formed about the periphery of base 19 is received within complimentary female detent 70 formed about the periphery of base holder 34. Attachment of the base 19 through the base holder 34 is analogous to attachment of the ultrasonic transducer to the transducer cup as disclosed in U.S. Pat. No. 4,913,155 issued to Dow et al. on Apr. 3, 1990, the disclosure of which are hereby incorporated by reference.

Reciprocating motion of the base 19, extension 18, and scanning ultrasonic transducer 16 is effected by a motor or driver comprising armature 30, containing permanent magnet 72, and electromagnet or stator 38. Stator 38 comprises two outwardly extending arms 39 and 40 diametrically disposed about armature 30 such that the flux lines developed thereby are generally oriented perpendicular to the flux lines of permanent magnet 72 when the armature 30 is in its centered or at rest position.

The armature 30 is rotatably or pivotally attached to the housing 11 via trunnions 46 which attach to the armature 30 via bearings 37 such that the armature 30 rotates or pivots about pivot axis 36. Trunnions 46 are supported by trunnion support 45 which extends upwardly from base 44. Trunnion support 45 comprises a split 47 and tensioning screw 59 such that the tension with which trunnion 46 is captured by trunnion mount 45 is adjustable. This arrangement also facilitates lateral position adjustment of the armature 30, and consequently of the base 19, extension 18 and scanning ultrasonic transducer 16. Those skilled in the art will recognize that various other mounting structures for the armature are likewise suitable. Base 44 rests upon support surface 48 of case 11 having threaded mount holes 49 formed therein such that fasteners, such as screws 50, pass through apertures 51 formed in the base 44 and thread into threaded holes 49 to attach the base 44, and consequently the armature 30 and stator 38 of the motor, to the housing 11.

Position sensor 60 is comprised of plate 61 and pickup 62 (best shown in FIG. 6). The plate 61 is rigidly attached to the armature 30 and rotates or pivots therewith such that a variable area of the plate 61 is received within and sensed by the coil 62 which is rigidly attached to the base 44. That is, the radius of the plate 61 varies with its angular position so that different quantities of the plate 61 area are disposed within the pickup coil 62 at different orientations of the armature 30. A detailed description of the position sensor is provided in U.S. Pat. No. 4,913,155.

Seal 52 (as shown in FIG. 6) is disposed with seal groove 58 (best shown in FIG. 3). The seal 52 facilitates leak free attachment of the cap 21 to the housing 11 such that the ultrasonic transmissive fluid remains contained therein.

The stator 38 is comprised of first 39 and second 40 arms which are alternatively magnetizable to define north and south poles to affect reciprocation motion of the armature 30. The stator 38 is comprised of coils 54 formed about laminated core 56. Semicircular cutouts 57 formed at the distal ends of arms 39 and 40 receive a portion of armature 30 to facilitate efficient flux linkage therewith. Leads 43 extend from the stator 38 through the handle 12 and join the cable 13.

Having thus described the structure of the ultrasonic peripheral vascular probe assembly the operation of the present invention may be described. Referring now to FIG. 7, operation of the motor of the ultrasonic peripheral vascular probe assembly of the present invention is schematically illustrated. Coils 54 are energized by leads 55 to alternately magnetize arms 39 and 40 of the laminated core 56 to define north and south poles such that each arm 39 or 40 alternately attracts the north and south poles of the magnet 72 disposed within the armature 30. Thus, the armature 30 is caused to rock or reciprocate in a rotating or pivotal motion, back and forth, about its axis. This reciprocating motion is communicated to the base 19 which is rigidly attached to the armature 30. The reciprocating motion is likewise communicated to the extension 18 and scanning ultrasonic transducer 16 formed upon the distal end of the extension 18. Thus, the scanning ultrasonic transistor 16 reciprocates back and forth about pivot axis 36 (as best shown in FIG. 5). Spring 31 (best shown in FIG. 6) provides a biasing force to constantly urge the armature 30 back to its centered or neutral position during operation.

When the scanning ultrasonic transducer 16 is positioned away from and out of the ultrasonic radiation path of doppler ultrasonic transducer 17, then doppler ultrasonic transducer 17 functions, i.e., radiates ultrasonic energy to effect fluid flow movement. When the scanning ultrasonic transducer 16 is positioned close to or within the ultrasonic radiation path of doppler ultrasonic transducer 17, doppler ultrasonic transducer 17 ceases functioning. Scanning ultrasonic transducer 16 and doppler ultrasonic transducer 17 are preferably operated on different frequencies to minimize acoustic interference therebetween.

Thus, to use the ultrasonic peripheral vascular probe assembly of the present invention, it is positioned in contact with the patient over the anatomical structure to be imaged such that the scanning ultrasonic transducer 16 moves along the longitudinal axis to the anatomical structure. Such positioning permits the present invention to effectively image over a greater area, generally elongate in configuration, than prior art devices. Thus, an image of the elongate anatomical structure as well as measurement of fluid flow therethrough is simultaneously provided by the present invention.

It is understood that the exemplary ultrasonic peripheral vascular probe assembly of the present invention described herein and shown in the drawings represents only a presently preferred embodiment of the invention. Indeed, various modifications and additions may be made to such embodiment without departing from the spirit and scope of the invention. For example, the scanning ultrasonic transducer can be configured and mounted in various ways to cause its motion to approximate straight line of linear motion. Indeed, its motion need not even be rotational pivotal. Rather various linear or generally linear motions are likewise suitable. Additionally, the cap may assume various configurations which reflect the motion of the scanning ultrasonic transducer and which minimize contact with the patient. Thus, these and other modifications and additions may be obvious to those skilled in the art and may be implemented to adapt the present invention for use in a variety of different applications.

What is claimed is:

1. A reciprocating drive motor comprising:
   (a) a stator having two arms;
   (b) at least one coil associated with said stator so as to induce a magnetic field therein;
   (c) an armature disposed intermediate the two arms of said stator, said armature having north and south magnetic poles;
   (d) at least one biasing member disposed within said armature, said biasing member biasing said armature in a generally centered position; and (e) wherein the coil(s) of said stator are energizable to produce a magnetic field of a first polarity so as to cause said armature to rotate to a first position and are also energizable to produce a magnetic field of a second polarity so as to cause said armature to rotate to a second position, movement of the armature back and forth between its first and second positions defining reciprocation thereof.

2. The reciprocating drive motor as recited in claim 1 wherein said armature comprises a permanent magnet.

3. The reciprocating drive motor as recited in claim 1 wherein said biasing member(s) comprise at least on spring.

4. The reciprocating drive motor as recited in claim 1 wherein said armature comprises a hollow tubular member having a permanent magnet disposed therein and having at least one spring biasing member disposed therein.

5. The reciprocating drive motor as recited in claim 1 further comprising adjustment means for varying the tension of said biasing member.

6. The reciprocating drive motor as recited in claim 1 wherein said biasing member comprises two opposing springs and wherein the tension applied by each spring is adjustable so as to vary the generally centered position of said armature.

7. The reciprocating drive motor as recited in claim 1 further comprising a position sensor associated with said armature for sensing the position thereof.

8. The reciprocating drive motor as recited in claim 7 wherein said position sensor comprises:
   (a) a plate rigidly attached to said armature such that said plate moves therewith;
   (b) a coil through which said plate moves; and
   (c) wherein the amount of said plate disposed with said coil depends upon the position of the armature.

9. A reciprocating direct drive motor for an ultrasonic probe assembly, said reciprocating direct drive motor comprising:
   (a) a generally U-shaped stator having two arms;
   (b) a coil disposed upon each of the two arms so as to induce a magnetic field therebetween;
   (c) an armature disposed intermediate the two arms, said armature comprising:
      (i) a hollow tubular member;
      (ii) a permanent magnet disposed within said hollow tubular member;
      (iii) two opposing springs applying tension to said armature disposed within said tubular member, said springs being adjustable so as to vary the position of said armature;
   (d) a position sensor associated with said armature for sensing the position thereof; and
   (e) wherein the coils of said stator are energizable to produce a magnetic field of a first polarity so as to cause said armature to rotate to a first position and are also energizable to produce a magnetic field of a second polarity so as to cause said armature to rotate to a second position, movement of the armature back and forth between its first and second positions defining reciprocation thereof.

10. A reciprocating drive motor comprising:
    (a) a stator having two arms;
    (b) at least one coil associated with said stator so as to induce a magnetic field therein;
    (c) an armature disposed intermediate the two arms of said stator, said armature having north and south magnetic poles, said armature comprising a hollow tubular member having a permanent magnet disposed therein and having at least one spring biasing member disposed therein, said biasing member biasing said armature in a generally centered position; and
    (d) wherein the coil(s) of said stator are energizable to produce a magnetic field of a first polarity so as to cause said armature to rotate to a first position and are also energizable to produce a magnetic field of a second polarity so as to cause said armature to rotate to a second position, movement of the armature back and forth between its first and second positions defining reciprocation thereof.

11. A reciprocating drive motor comprising:
    (a) a stator having two arms;
    (b) at least one coil associated with said stator so as to induce a magnetic field therein;
    (c) an armature disposed intermediate the two arms of said stator, said armature having north and south magnetic poles;
    (d) at least one biasing member associated with said armature, said biasing member biasing said armature in a generally centered position;
    (e) a position sensor associated with said armature for sensing the position thereof, said position sensor comprising:
       (i) a plate rigidly attached to said armature such that said plate moves therewith;
       (ii) a coil through which said plate moves; and
       (iii) wherein the amount of said plate disposed within said coil depends upon the position of the armature; and
    (f) wherein the coil(s) of said stator are energizable to produce a magnetic field of a first polarity so as to cause said armature to rotate to a first position and are also energizable to produce a magnetic field of a second polarity so as to cause said armature to rotate to a second position, movement of the armature back and forth between its first and second positions defining reciprocation thereof.

* * * * *